US006847446B2

United States Patent
Shilling

(10) Patent No.: US 6,847,446 B2
(45) Date of Patent: Jan. 25, 2005

(54) CHEMICAL ANALYSIS AND DETECTION BY SELECTIVE ADSORBENT SAMPLING AND LASER INDUCED BREAKDOWN SPECTROSCOPY

(75) Inventor: Billy J. Shilling, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 50 days.

(21) Appl. No.: 10/395,130

(22) Filed: Mar. 25, 2003

(65) Prior Publication Data

US 2004/0189990 A1 Sep. 30, 2004

(51) Int. Cl.$^7$ ............................ G01N 21/63; G01N 1/00
(52) U.S. Cl. ........................................ 356/318; 356/36
(58) Field of Search ............................ 356/36, 38, 317, 356/318

(56) References Cited

U.S. PATENT DOCUMENTS 3,653,773 A * 4/1972 Childs ........................ 356/38
3,654,801 A * 4/1972 Keefer et al. ................ 356/38
3,832,060 A * 8/1974 Dahlquist .................... 356/36
4,220,414 A * 9/1980 Barringer .................... 356/318
4,561,777 A * 12/1985 Radziemski et al. ........ 356/318

* cited by examiner

Primary Examiner—F. L. Evans
(74) Attorney, Agent, or Firm—John J. Karasek; John Gladstone Mills, III

(57) ABSTRACT

The present invention describes an apparatus capable of specific detection of environmental chemicals in water and air. The apparatus combines a specific chemical sampler, encompassing selectively adsorbing material to automatically sample air or water samples and trap target chemicals, and uses Laser Induced Breakdown Spectroscopy for analysis of trapped chemicals. Operation of the apparatus is controlled by a computer interface. In order to provide the accuracy needed for chemical detection and adaptability required for field use it is required to incorporate Laser Induced Breakdown Spectroscopy with sample collection utilizing selective adsorbents. The invention provides a chemical detection device for concentrating chemical samples from water or air environments and then analyzing these samples with a low power highly portable Laser Induced Breakdown Spectroscope.

14 Claims, 4 Drawing Sheets

CHEMICAL ANALYSIS AND DETECTION BY SELECTIVE ADSORBENT SAMPLING AND LASER INDUCED BREAKDOWN SPECTROSCOPY

BACKGROUND OF THE INVENTION

1. Field of the Invention

This invention relates to an apparatus for the detection and identification of chemicals by selective adsorption or entrapment of chemicals onto a matrix, subsequent analysis and identification of adsorbed or entrapped chemicals by spectroscopy and graphic display of analysis results.

More specifically, this invention relates to an apparatus for the detection of specifically targeted chemical species by combining laser induced breakdown spectroscopy (LIBS) with a selectively adsorbing polymer containing surface integrated into a sampling apparatus with computer control and display interface.

2. Description of the Prior Art

Field deployable and laboratory based chemical detection systems are needed in industry, military and civilian government for use in a wide range of possible scenarios ranging from identification of environmental contaminants to detecting use and possible exposure of populations to chemical agents. An important aspect is the requirement for not only accurate and reliable detection but also for a detection device that operates sensitively, rapidly and reliably with minimal human intervention. Several approaches to chemical detection are currently in use with most centered on detection of chemicals in air and water samples. However, the most widely used in industry and government, to date, are devices encompassing Ion Mobility Spectrometry (IMS) and surface acoustic wave (SAW) sensor technology.

A typical IMS device comprises an ion reaction chamber, an ionization source, an ion drift tube, a shutter to allow ions into the drift tube and a Faraday plate for the collection of ions at the end of the drift tube. A carrier gas, normally air or nitrogen at atmospheric pressure, transport gases or vapors from the material to be analysed into the ionization chamber of the ion mobility spectrometer (See Clemmer and Jarrold, Ion Mobility Measurements and their Applications to Clusters and Biomolecules, Journal of Mass Spectrometry, Vol. 32, p. 577 (1997).

IMS devices operate by drawing in air samples whereby the chemical constituents are ionized by sources such as beta radiation, lasers, discharge lamps or partial or corona discharges, forming low-energy stable, charged molecules (ions). The ions are then accelerated by their transduction through the discharge tube, where their mobility is measured as the ions make collisions with the buffer gas. The movement through the gas produces a constant drift velocity for each type of ion. The mobility is the ratio of the drift velocity to the electric field and contains information about the interaction between the ion and the buffer gas. For large polyatomic ions, the mobility is dependent on the average collision cross-section. Mobility measurements can be used to separate ions with different geometries and several groups have used these measurements to characterize the size distribution of aerosol particles. IMS devices when used with pyrolysis upstream of the IMS detector, have been employed for the identification of bacterial agents, as well as chemical agents. (See Clemmer and Jarrold, supra.)

Surface Acoustic Wave sensors (SAW) operate by measuring changes in the properties of acoustic waves, created by changes of the surface-attached matter, as they travel at ultrasonic frequencies in piezoelectric materials. Agent classes can be identified by applying pattern recognition algorithms. Although these systems have been successfully utilized to detect and quantify chemicals in air samples, they suffer from deficiencies including sensitivity to humidity and interference from contaminants leading to false positive responses and incorrect identification and quantification of the chemicals present. Instrumentation for the rapid analysis of large biomolecules and mixtures of organic and inorganic molecules using IMS is described in U.S. Pat. No. 6,323,482 to Clemmer, et al.

Other detection systems include electrochemical sensors, flame photometry, thermoelectric conductivity, infrared spectroscopy, Fourier transform infrared spectrometry and Raman spectroscopy have had varying levels of success in chemical detection. Mass spectrometry is effective at reliably identifying chemical constituents but is relatively complex, requires considerable sample preparation and power requirements, which is untenable for normal field operation. Furthermore, none of the above systems can be utilized under water. Therefore, a need exists for accurate and reliable detection systems capable of operating under field conditions with minimal power requirements.

Another detection system is Laser Induced Breakdown Spectroscopy (LIBS). This spectroscopy is an analytical technique that utilizes high pulsed, high powered laser to vaporize a small volume of matter. (D. A. Cremers et al, Spectrochemical Analysis of Liquids Using the Laser Spark, Applied Spectroscopy, Vol. 38, p. 721 (1984). The vaporization causes disassociation of molecular bonds forming polyatomic ions or elements in excited states. The excited polyatomic ions or elements then return to their ground state by a decay process. During the decay process, the elements emit photons of energy, i.e., fluorescent emissions of light. The wavelengths in the emission are analyzed to determine the identity of the elements in the vaporized material. Generally, the intensity of the fluorescent emissions is proportional to the concentration of the element in the sample. LIBS has been used to analyze solids (See Aguilera et al, Determination of Carbon Content in Steel Using Laser Induced Breakdown Spectroscopy Applied Spectroscopy, Vol. 46, p. 1382 (1992); Grant, et al; Quantitative Elemental Analysis of Iron Ore by Laser Induced Breakdown Spectroscopy, Applied Spectroscopy, vol. 45, p. 701 (1991); and Ottesen, et al., Real-Time Laser Spark Spectroscopy of Particulates in Combustion Envimments, Applied Spectroscopy, vol. 43, p. 967 (1989)) and liquids (Cremers et al, Spectrochemical Analysis of Liquids Using the Laser Spark, Applied Spectroscopy., vol. 38, p. 721 (1984)). U.S. Pat. No. 5,757,484 to Miles, et al describes a standoff laser induced breakdown spectroscopy system for in situ identification of soil contaminants, which is not in contact with the material under analysis. Additionally, U.S. Pat. No. 6,366,353 to Brown, et al describes an apparatus using LIBS to identify constituents and their concentration on coated substrates, typically fiber optic cores or similar substrate.

SUMMARY OF THE INVENTION

An object of this invention is an apparatus capable of detecting and identifying chemical compounds accurately and with a low false detection rate. An aspect of the apparatus is that it is capable of being operated manually or in automatic mode as a remote detection apparatus. Further, the apparatus will be capable of battery power operation for field detection operation.

It is an another object of the invention to provide an accurate chemical detecting and identification apparatus capable of operating on very small sampling surfaces and with the capability of interrogating a surface numerous times during a measurement period.

A still further object of the invention is providing a chemical detection and identification material that selectively adsorbs target chemical compounds. An aspect of the invention is that selectively adsorbing material is deposited onto a movable surface to enable continuous collection of samples drawn in either as air samples or water samples. An aspect of the selectively adsorbing material is that it can remain exposed and be sampled numerous times and then be archived for later analysis by other means when a new sample surface is moved into place by the collection mechanism in the selective adsorbtion sampler. Additionally, the adsorbent surface may incorporate different adsorbent material, selective for specific classes of chemicals, deposited in different quadrants of the surface in order to permit simultaneous adsorbency of different target chemicals.

Another object of the invention is that the invention will contain an efficient sample collection system capable of sampling air or water samples for deposition of target chemicals onto the selectively adsorbing material. The sample collection system provides input of either air or water samples in a sufficiently sized flume to permit passage of the air or water sample. The air or water is moved through the flume by a variable speed propeller fan that provides flow past the adsorbent material. An additional object is the capability to sensitively detect and accurately identify samples collected on the selectively adsorbing surfaces. Analysis of specifically targeted chemicals will be conducted by laser induced breakdown spectroscopy (LIBS).

A still further object of the apparatus is the optical accessibility of the laser and LIBS spectrophotometer(s) to the selectively adsorbing surface. The lasers are used for liberation of compounds and for excitation or stimulation to produce fluorescence. The LIBS spectrometer(s) will provide wide coverage of the visible and the ultraviolet spectrums for maximum versatility of chemical analysis.

A still further object of the invention is the ability to control the apparatus in manual as well as automatic mode for remote chemical detection. The apparatus will be computer controlled and configured to permit updating of computer hardware and software. The control computer will permit either manual operation or automatic operation. Statistical modeling will be integrated into the control computer software to permit pre-selectable sampling programs for manual and automatic operation that will provide variable thresholds of detection appropriate for the target chemical species being measured. Manual and automatic operation will use computer assisted analysis to identify and estimate the concentration levels of the targeted chemical species. The statistical modeling will incorporate optimum strategies for flow rate, number of LIBS interrogations of the surface during selected measurement periods and time between measurement periods for chemical species of interest. The use of battery power and its impact on efficient operation will also be incorporated into the detection and sampling system in remote operation.

These and additional objects of the invention are accomplished by an apparatus incorporating a selective adsorbtion sampler SAS, which deposits target chemicals onto selectively adsorbent materials incorporated onto a movable surface, a laser induced breakdown spectrometer LIBS, for chemical analysis of target chemicals along with computer hardware and software for manual or remote (automatic) operation.

DETAILED DESCRIPTION OF THE PREFERRED EMBODIMENT

A more complete appreciation of the invention will be readily obtained by reference to the following Description of the Preferred Embodiments and the accompanying drawings. The representations in each of the figures is diagrammatic and no attempt is made to indicate actual scales or precise ratios. Proportional relationships are shown as approximations.

Having described the invention, the following examples are given to illustrate specific applications of the invention including the best mode now known to perform the invention. These specific examples are not intended to limit the scope of the invention described in this application. Obviously, many modifications and variations of the present invention are possible in light of the above teachings. It is therefore to be understood that, within the scope of the appended claims, the invention may be practiced otherwise than as specifically described.

The apparatus is a detection device that selectively binds and detects target chemicals in air or fluid samples. Samples are collected via the selectively adsorbing sampler (SAS) via a sample collection component which includes a single or multiple chemoselective polymers capable of adsorbing specific target chemicals including those used on surface acoustic wave devices (SAW devices) as described in U.S. Pat. No. 6,336,368 to Chung et al. The polymer(s) is layered on the surface of a sheet of inert, flexible material and is exposed to the flow to be sampled and analyzed. The surface containing polymers exposed to the sample, are then analyzed by the Laser Induced Breakdown Spectroscope (LIBS).

The identity of elements is determined by measurement of wavelength of fluorescence emission of excited molecules, energized by a high energy laser. The lasers in the apparatus are either single or multiple high energy lasers capable of producing a LIBS plasma. Any repetitive pulse rate over a wide pulse width, from femtosecond to microseconds, can be utilized in the apparatus. A list of possible lasers include, but are not limited to ArF at 193 nm, KrF at 248 nm, Nd:YAG lasers at 1064 nm, 532 nm, 355 nm, or 266 nm., pulsed argon or krypton lasers, copper vapor lasers, $CO_2$ lasers and Ti: sapphire lasers.

Figure 1:
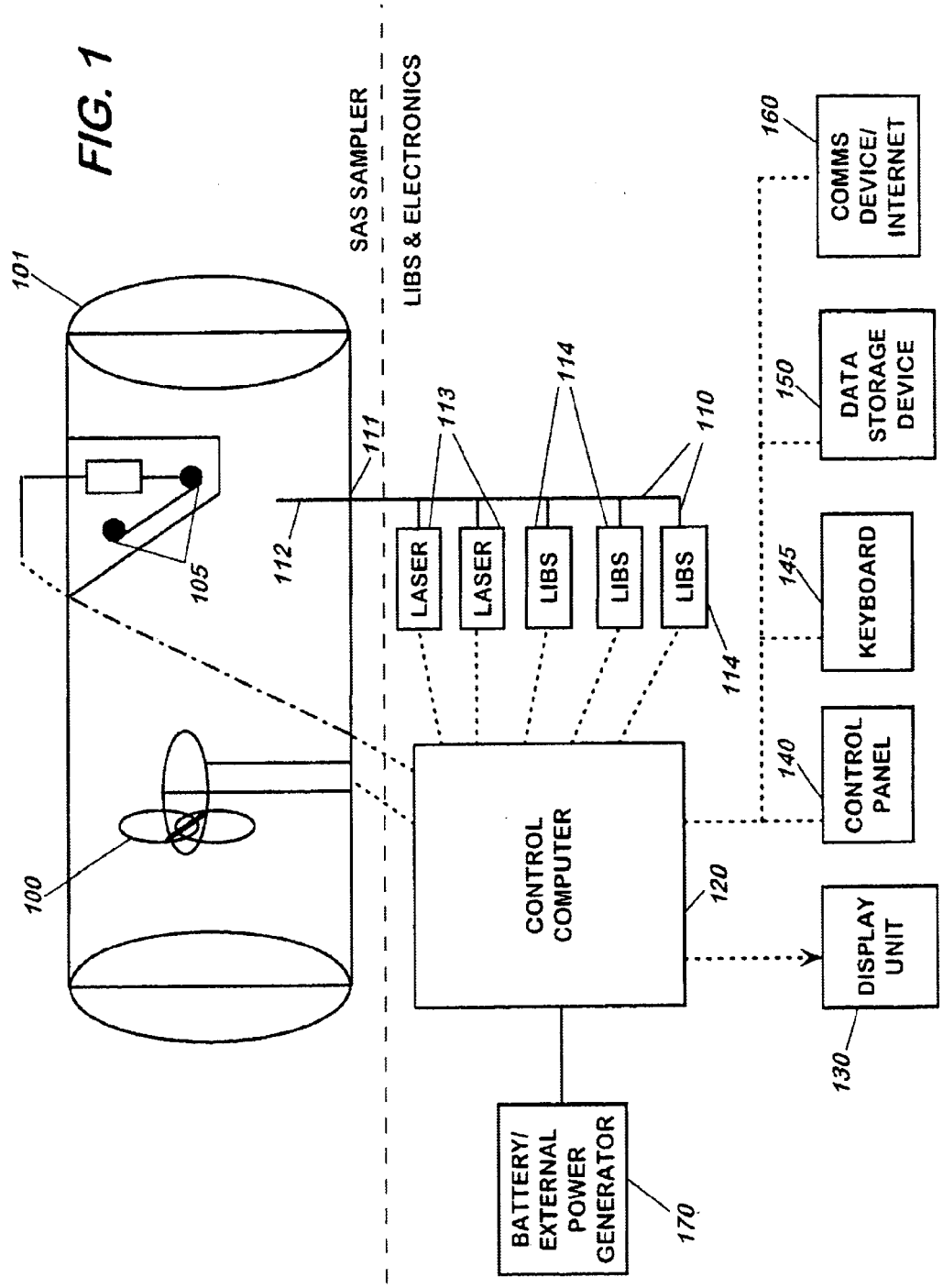
FIG. 1 is a schematic block diagram of an embodiment of the invention of a selective adsorbtion sampler with laser induced breakdown spectroscope.

Referring to FIG. 1, a preferred embodiment of the invention includes a selective adsorbing sampler (SAS) 101, containing a propeller fan 100 for inducing flow of either air, or other gas media, or fluid, such as water, and a movable collection component 105, situated at about a 45° angle from the plane of flow. The SAS is optically connected via fiber optical cables 110 connected to one or more lasers 113 and one or more LIBS spectrophotometers 114. The SAS end of the fiber optic cables enters the SAS through a sealed opening 111 in the SAS outer container. It extends toward the selectively adsorbing surface 105 and ends in close proximity to the surface 112.

The fiber optic cable is close enough to the adsorbing surface to efficiently detect fluorescent emissions yet distant enough so as to not impede the flow over the adsorbing surface. Typically, this is approximately 10 inches but can be further or closer. The SAS, laser(s) and LIBS spectrophotometers are electrically and operatively connected to a control computer 120 containing a display unit 130, control panel 140 and keyboard 145. Additionally, the control computer 120 is electrically and operatively connected to the SAS and is capable of controlling the movement of the selectively adsorbing surface 105 of the sample collection component and also controlling the rate of flow over the adsorbing surface by controlling the operation of the fan propeller 100. The control computer also presents data and analysis results to the operator through the display unit 130.

Figure 2:
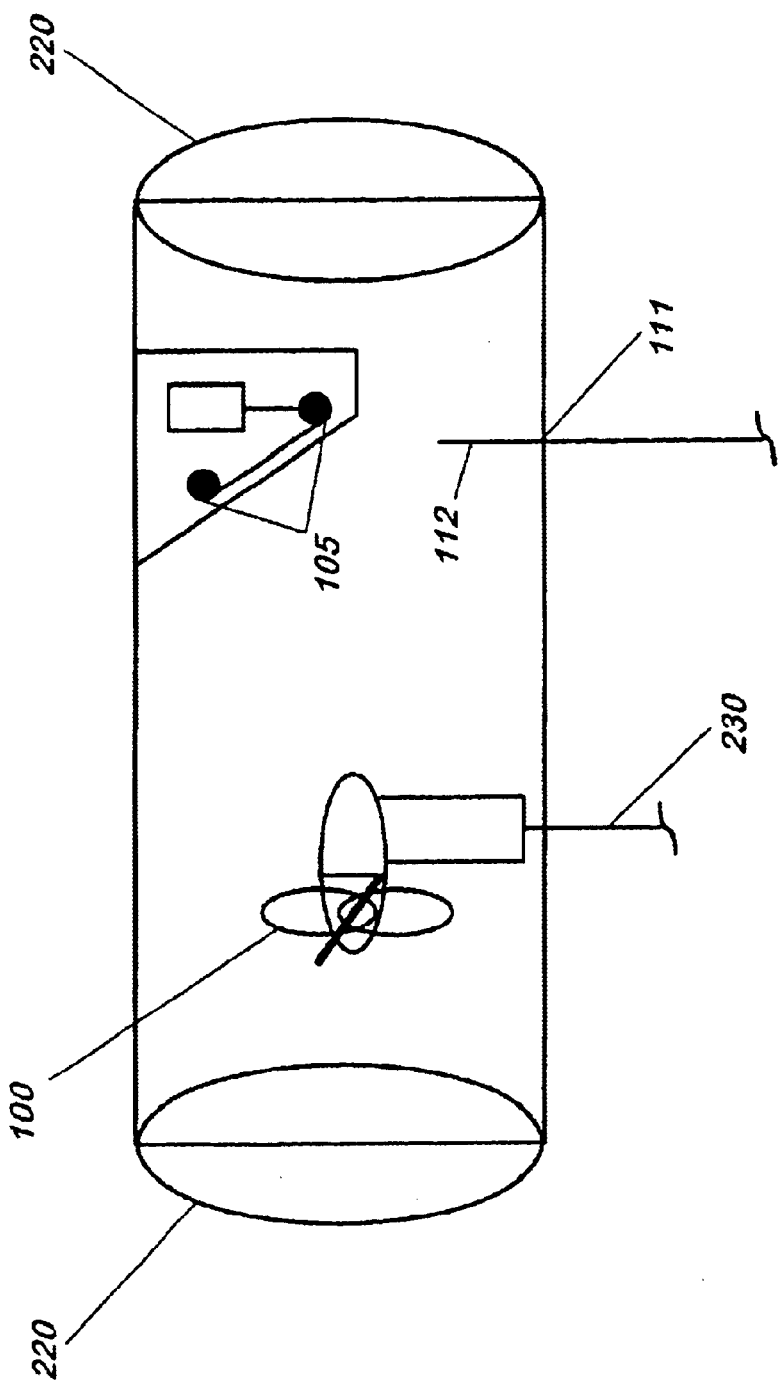
FIG. 2 is a schematic block diagram of the selective adsorbent sampler.

FIG. 2 shows a block diagram of the selective adsorbtion sampler (SAS) of the invention. The embodiment of the apparatus contains a SAS for collection of air or water samples. A fan propeller 100, shielded by wire or similar screen 220, provides motive force to impart either air or water movement into the SAS flume that directs movement of the sample fluid over the movable adsorbent surface 105. Target chemicals are then selectively bound to selectively adsorbing materials attached to the movable surface 105. External to the propeller is a mesh screen 220 configured to promote free movement of air past the propeller yet prevent entry into the SAS of relatively large objects which might damage the internal components of the SAS. The fan 100 is operatively connected by an electrical connection to the control computer 120 permitting the fan to be run at variable speeds thus controlling the flow rate of the air over the adsorbing surface 105.

Figure 3:
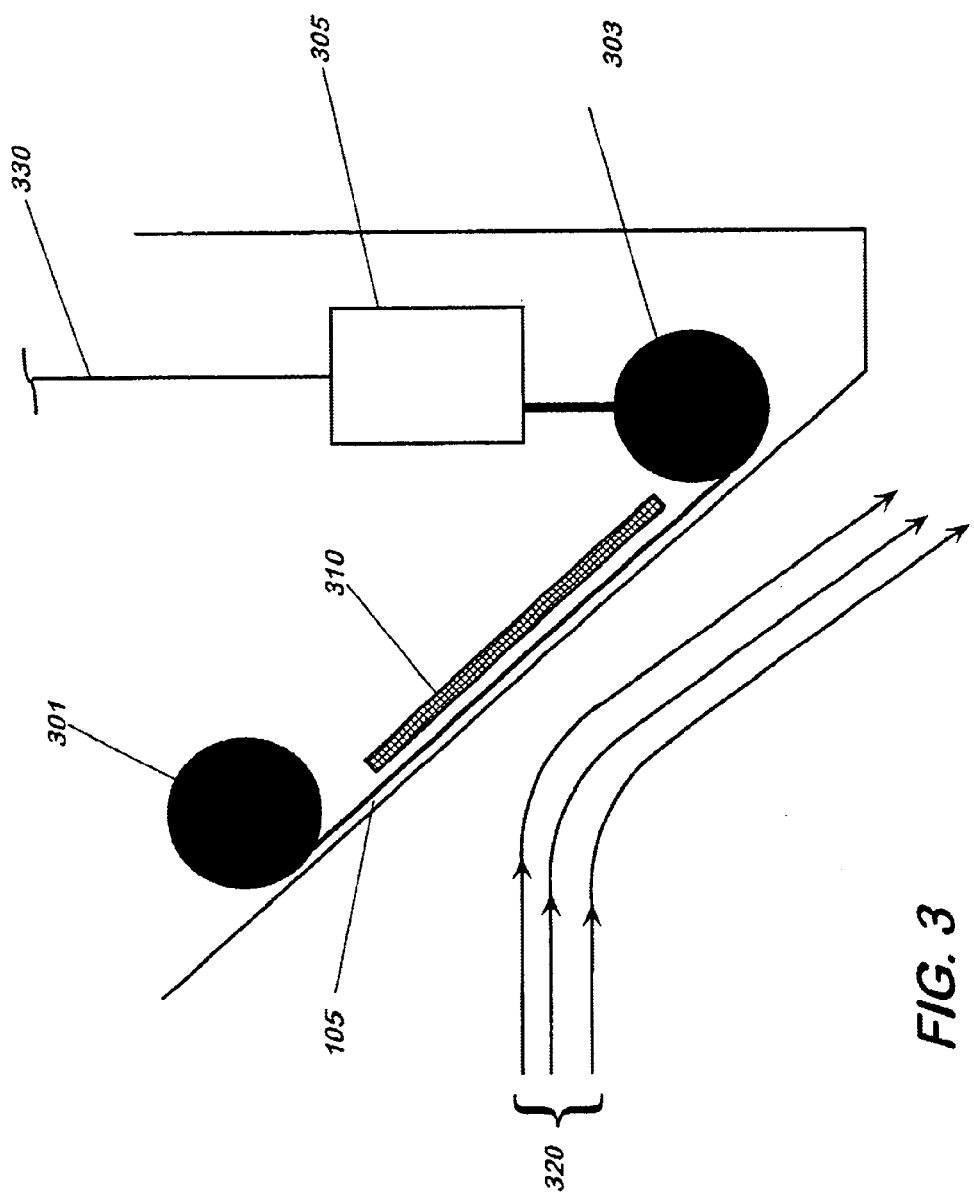
FIG. 3 is a schematic block diagram of the mechanism controlling the advancement of the selective adsorbent surface contained in the sampler.

FIG. 3 shows a block diagram of the movable adsorbtion surface. In an embodiment of the apparatus, the sample collection component's movable adsorbtion surface is composed of two rollers, one to store surface material 301 and another to receive selectively adsorbing surface portions that have been exposed to the incoming sample 303. The selectively adsorbing surface is supported by a stiff support 310. The sample collection component also contains a motor that is movably connected to one of the rollers in order to scroll the selectively adsorbing surface over the stiff support 310 and expose the surface to the sample. The flow of air or fluid sample containing target chemical is shown as 320. The sample collection component is operatively connected 330 to the control computer 120 which is capable of varying the motor speed, including stopping the motor, and therefore the length of time the selectively adsorbing surface 105 is exposed to collect a sample.

In another embodiment the apparatus the SAS is configured for input of liquid samples. Fluid movement into the flume is imparted by the propeller fan 100. Furthermore, the optical connection 111 to the SAS is via a water-tight connection through the outer wall of the SAS.

Another embodiment relates to the power supply of the invention of the Selective Adsorbtion Sampler with Laser Induced Breakdown Spectroscope. In addition to being operated and powered by normal household current, the invention can also be operated as an independent, stand-alone unit powered by a portable battery or external power generating source 170. The apparatus can store data in an attached data storage device 150 or can be linked via internet or similar data connection link 160 for remote data access and storage.

Figure 4:
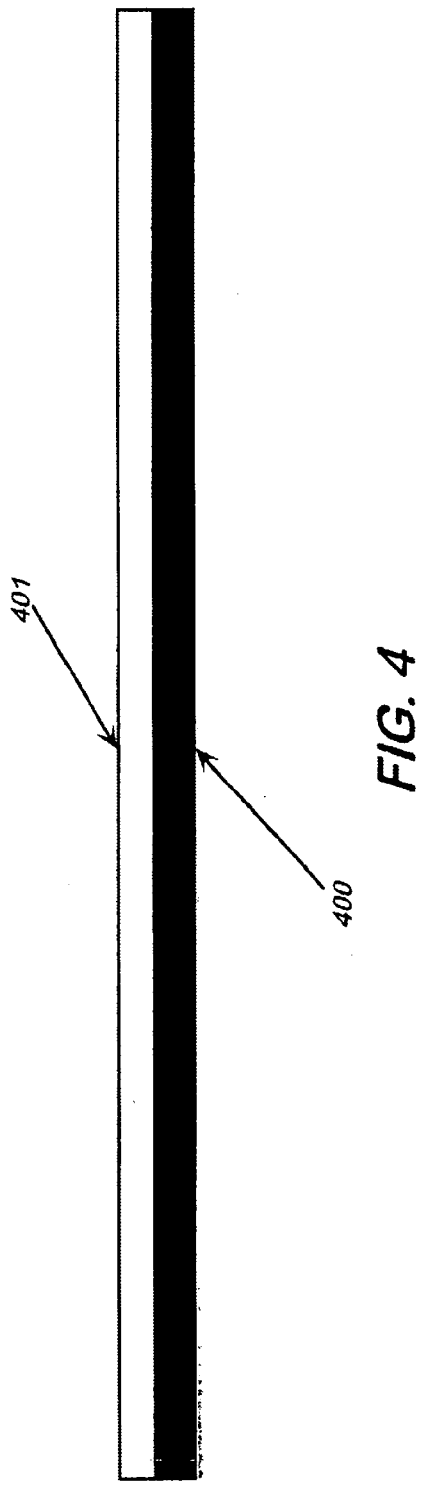
FIG. 4 is a lateral view of the selectively adsorbing surface.
Figure 5:
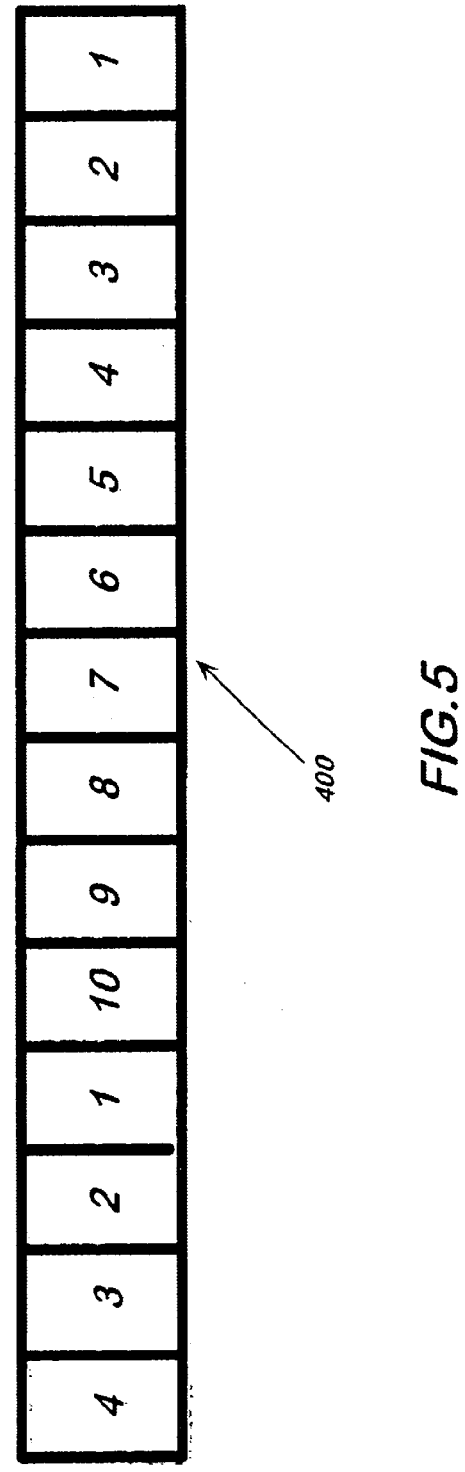
FIG. 5 is a top view of the selectively adsorbing surface, indicating different adsorbing polymers 1 through 10.

Referring to FIG. 4, in a further embodiment the selectively adsorbing surface is uniformly coated with a single selectively adsorbing polymer such as polyethylene. Alternatively, referring to FIG. 5, the inert backing surface 400 can be coated with multiple selectively adsorbing polymers numbered 1 through 10 to enable selective capture of multiple chemicals. In this embodiment as the surface moves past the optical cable, adsorbed chemicals are ionized and analyzed, in turn, as the sheet containing the adsorbing polymer progresses past the end of the optical cable. Therefore, as indicated in FIG. 5, polymer 1 would be exposed to the incoming sample then the adsorbed chemical analyzed as it progresses past the optical cable. Subsequently, as the surface moved past the optical cable, polymer 2, 3, and following would, in turn, be analyzed.

Although this invention has been described in relation to an exemplary embodiment thereof, it will be understood by those skilled in the art that still other variations and modifications can be affected in the preferred embodiment without detracting from the scope and spirit of the invention as described in the claims.

What is claimed is:

1. A chemical detection device comprising:
   a conduit for moving a fluid over a selectively adsorbing surface;
   said surface adsorbing chemical samples from said fluid;
   a laser for vaporizing said chemical samples on said selectively adsorbing surface;
   a laser induced breakdown spectrometer for analyzing said chemical samples.

2. The chemical detection device of claim 1 further comprising:
   a propeller fan for moving said fluid at different rates through said conduit.

3. The chemical detection device of claim 1 further comprising:
   a motor for moving said selectively adsorbing surface.

4. The chemical detection device of claim 2 further comprising:
   a computer for controlling the speed of said propeller fan for varying the rate of flow of said fluid past said selectively adsorbing surface.

5. The chemical detection device of claim 3 further comprising:
   a computer for controlling the speed of said motor for selectively moving said selectively adsorbing surface.

6. The chemical detection device of claim 1, further comprising:
   a computer operatively connected to said laser and to said laser induced breakdown spectrometer for controlling said laser and said laser induced breakdown spectrometer.

7. The chemical detection device of claim 6, further comprising:
   a display, a control panel, a keyboard, and a data storage device operatively connected to said computer.

8. The chemical detection device of claim 7, further comprising:
   a data communications link operatively connected to said computer and to said data storage device.

9. The chemical detection device of claim 1, further comprising:
   a protective screen mounted on the front and back of said conduit.

10. The chemical detection device of claim 1, further comprising a chemical sample collection component with said selectively adsorbing surface mounted on two rollers, with one roller attached to the leading end of said adsorbing surface and the other roller attached to the trailing end of the adsorbing surface, so that the said selectively adsorbing surface is moved and wound from one roller to the other roller.

11. The chemical detection device of claim 4 further comprising:

a data communications link between the internet and said computer.

12. The chemical detection device of claim 1 further comprising:

a chemical polymer coating on said selectively adsorbing surface for selective capture of chemical samples.

13. The chemical detection device of claim 1 further comprising:

multiple chemical polymer coatings on an said selective adsorbing surface for selective capture of multiple chemical samples.

14. A method of using a chemical detection device comprising the steps for:

moving a fluid through a conduit over a selectively adsorbing surface;

causing said selectively adsorbing surface to adsorb chemical samples from said fluid;

vaporizing through laser pulses said chemical samples on said selectively absorbing surface by laser;

analyzing said chemical samples by means of laser induced breakdown spectroscopy.

* * * * *